(12) United States Patent
Li (10) Patent No.: US 8,480,574 B2
(45) Date of Patent: Jul. 9, 2013

(54) FLEXIBLE DAM AND RETRACTOR

(75) Inventor: Jiangming Li, Shijiazhuang (CN)

(73) Assignee: Empire Technology Development LLC, Wilmington, DE (US)

( * ) Notice: Subject to any disclaimer, the term of this patent is extended or adjusted under 35 U.S.C. 154(b) by 408 days.

(21) Appl. No.: 12/770,120

(22) Filed: Apr. 29, 2010

(65) Prior Publication Data
US 2011/0270039 A1    Nov. 3, 2011

(51) Int. Cl.
*A61B 1/32*    (2006.01)

(52) U.S. Cl.
USPC .......................................................... 600/206

(58) Field of Classification Search
USPC ............................ 433/136–139; 600/201–246
See application file for complete search history.

(56) References Cited

U.S. PATENT DOCUMENTS

| | | | |
|---|---|---|---|
| 2,092,549 A * | 9/1937 | Craigo | 433/136 |
| 3,396,468 A * | 8/1968 | Dayhoff | 433/93 |
| 4,004,345 A * | 1/1977 | Ely | 433/139 |
| 4,600,387 A * | 7/1986 | Ross | 433/136 |
| 4,992,046 A * | 2/1991 | Sharp | 433/93 |
| 5,152,686 A * | 10/1992 | Duggan et al. | 433/93 |
| 5,340,313 A * | 8/1994 | Hussin | 433/136 |
| 6,024,564 A * | 2/2000 | Kesling | 433/72 |
| 6,093,022 A * | 7/2000 | Swallow | 433/136 |
| 6,299,446 B1 * | 10/2001 | Ahlers | 433/136 |
| 6,575,749 B1 * | 6/2003 | Greenwald | 433/141 |
| 6,648,642 B1 * | 11/2003 | Horvath et al. | 433/136 |
| 7,044,738 B2 * | 5/2006 | Cox | 433/136 |
| 7,465,167 B2 * | 12/2008 | Haje | 433/136 |
| 2004/0209224 A1 * | 10/2004 | Heasley | 433/139 |
| 2006/0177796 A9 * | 8/2006 | Heasley | 433/136 |

* cited by examiner

*Primary Examiner* — Kevin T Truong
*Assistant Examiner* — Christopher Beccia
(74) *Attorney, Agent, or Firm* — Maschoff Brennan (57) ABSTRACT

An instrument for field isolation during surgery. The instrument includes a flexible member, and a retractor configured to retract the flexible member for field isolation during a surgical procedure. A method of providing field isolation during a surgical procedure is also provided.

4 Claims, 6 Drawing Sheets

FLEXIBLE DAM AND RETRACTOR

TECHNICAL FIELD

Embodiments described herein relate to medical instruments and methods of treatment.

BACKGROUND

Providing a zone of isolation in a surgical environment can facilitate an operation as well as facilitate post-operative healing. For example, in dental operations such as root canals and/or root canal retrofilling, isolation is desirable because of the potential for contamination from saliva and effusion from the bone wall around lesion zone. This can make it very difficult to keep the work zone dry. Also, a moist oral environment is conducive to bacterial growth. Additionally, the effusion and/or saliva can form a thin liquid layer between the obturation materials (i.e., refilling materials) and the bone wall, which can result in post-operation micro leakage, gap formation, and failure of the treatment.

At the same time, the detritus, which is produced during the process of filling, drilling, and the apex removal, can fall into the bone cavity. Detritus that falls into the bone cavity can be difficult to remove and can act as a source for post-operative infection.

SUMMARY

According to an aspect of the medical devices described herein, an instrument for field isolation during surgery includes a flexible member. In one aspect, the flexible member can include a flexible membrane. A retractor is used to retract the flexible member.

According to another aspect, an instrument for field isolation during oral surgery includes a flexible dam membrane having a periphery and a frame attached to the periphery of the membrane. The frame can be configured to fit at least one periapical structures, such as but not limited to a vestibular groove. A refractor is coupled to the frame of the flexible dam and retracts the flexible dam, lip tissues, and/or gum tissues to expose at least a portion on an oral structure for treatment.

According to another aspect, an instrument for isolation of a root apex during an oral procedure includes a flexible dam membrane having a periphery and a frame attached to the periphery of the membrane. The frame is configured to fit periapical structures. A retractor is coupled to the frame of the flexible dam and has a body and an arm member having an adjustable angle. A widened portion positioned on the arm is configured to retract lip tissues, and/or gum tissues to expose the root apex of a tooth for treatment. A retaining member retains the flexible dam around a root apex. The retaining member includes a shaft having an end structure configured to retain the flexible dam around the root apex.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

The foregoing and other features of the present disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

FIGS. 3A-3D illustrate various aspects of a retractor in accordance with another embodiment of a medical device, in which

FIGS. 4A-4E illustrate various aspects of a retractor in accordance with yet another embodiment of a medical device, in which

DETAILED DESCRIPTION OF EMBODIMENTS

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

In one embodiment, medical devices described herein can include an instrument for field isolation during surgery. That is, the medical device can include an instrument configured for isolating a work area during a surgical procedure, such as, but not limited to, isolating an opening in a patient's body, a maxillofacial area, an oral area, an oral area around an exposed portion of a tooth, or the like. In one aspect, the instrument for field isolation during surgery can include a flexible member and a retractor. The flexible member can be configured to provide field isolation in the work area during the surgical procedure. Similarly, the retractor can be configured to function cooperatively with the flexible member to maintain positioning of the flexible member in the work area and to retract tissues in the work area to facilitate field isolation.

In one aspect, the flexible member can include a flexible membrane such as a latex rubber membrane, a flexible thermoplastic polymer membrane, a silicone rubber membrane, or other suitable materials with suitable resilience and tension. In one aspect, the flexible member can further include a flexible membrane and a frame. In one aspect, the flexible membrane can be stretched over the frame or otherwise coupled to the frame by adhesive, sonic welding, integral molding, and the like.

In one aspect, the frame may be made of the same materials as the flexible membrane. However, in other aspects, the frame may be made of a different material from that of the flexible membrane, such as metallic materials, which include but are not limited to aluminum, titanium, steel, alloy thereof, and the like, or plastic materials.

In one aspect, the flexible member and the retractor are configured for isolation of an oral area during an oral procedure. For example, the field isolation instrument can be used to provide isolation during an oral procedure such as a periodontal procedure, an endodontic procedure (e.g., a root canal), root end surgery (e.g., apicoectomy), or tooth extraction, and the like. As such, the retractor can be configured to retract lip and gum tissues and/or expose a tooth portion, such as a root apex portion of a tooth for treatment in a root end surgical procedure.

In some embodiments, the retractor may be a retracting member integral with the frame, which is configured to retract lip and gum tissues while helping to maintain the positioning of the flexible member to expose a tooth portion for treatment. In some embodiments, the retracting member may be of essentially any shape (e.g., a substantially cylindrical shape) extending from the periphery of the frame at essentially any angle relative to a plane defined by the frame (e.g., substantially perpendicular). In some embodiments, the length of the retracting member may range, for example, without being limited to, from about 10 mm to about 300 mm, or from about 20 mm to about 300 mm, or from about 50 mm to about 300 mm, or from about 100 mm to about 300 mm, or from about 200 mm to about 300 mm, or any length therebetween.

In one aspect, the frame can be configured to fit periapical structures around the root of a tooth. In another aspect, the frame can be configured in a curved plane to fit in a vestibular groove, which is a groove-shaped depression in the jaw above the gum line on the labial side of the teeth (i.e., the side of the teeth facing the lips). As such, in some embodiments, the frame may be configured in a plane shaped of substantially circular in cross section, the diameter dimension of which may range, for example, but not being limited to, from about 1.5 cm to about 3 cm. In some alternative embodiments, the shape of the frame may be a geometry other than a circle, including, but not being limited to, an oval, square, oblong, triangle, trapezoid, and the like, depending on the particular applications. In some other embodiments, the frame may be configured in a curved plane with a spatial profile to fit in the vestibular groove or other periapical structures. In some embodiments, the frame may be shaped like a saddle, which has a middle plane and two wing planes extending at either end of the middle plane in a direction inclined with respect to the middle plane.

In one aspect, the flexible member can include an orifice configured to grip a tooth. For example, the orifice can be a hole, a slit, a pair of slits arranged in an x shape, or another structure formed in the flexible membrane that is configured to allow the flexible membrane to surround a tooth or another work area and isolate it from the surrounding area. For example, the orifice in the flexible member can be used to surround a tooth or a portion of a tooth and thereby isolate the tooth or the portion of the tooth from the rest of the oral environment. In one aspect, the orifice can be an apex gripping orifice configured to grip the apex portion of a tooth.

In one aspect, the instrument for field isolation can further include a retaining member configured to retain the flexible member around an exposed portion of a tooth. The exposed portion can be a naturally exposed portion (e.g., the portions of the teeth that are naturally visible), or the exposed portion can be a portion of a tooth that is exposed during an oral procedure such as a root apex, or the exposed portion can be a portion of the oral anatomy that is exposed during an oral procedure such as a vestibular groove, or the like. In one aspect, the retaining member can include a shaft having a first end, the first end including a first structure configured to retain the flexible member around the tooth. In one aspect, the first structure configured to retain the flexible member around the tooth can include, for example, an at least partially circumscribed opening such as a loop-shaped structure including, but not limited to, a closed loop, an open loop, or the like. In another aspect, the first structure configured to retain the flexible member around the tooth can include, for example, a straight or curved extension of the first end. In one aspect, the shaft can further include a second end, with the second end including a second structure configured to retain the flexible member around the tooth, a portion of a tooth (e.g., the root apex), several teeth, or the like.

In one aspect, the flexible member can further include a connector member configured for removably attaching the retractor to the flexible member. In one aspect, the retractor can include a body and an arm member. For example, the flexible member can include an orifice or a recess configured to receive and hold an arm member extending from the retractor. In some embodiments, the retractor can include a main body of substantially cylindrical shape with a first end and a second end, and an arm member of substantially cylinder shape with an arm body and an arm connection portion at one end thereof. The other end of the arm member can be attached to the main body at the first end thereof through an optional transition taper portion, a pivotable portion, or the like.

In some embodiments, the arm connection portion of the arm member can include a complementary configuration with the connector, by means of which the arm member may be engaged with the connector of the flexible dam. In some embodiments, the manner for the connection of the connector and the arm connection portion may be threading, shape locking, and the like, depending on particular applications. In this case, corresponding connecting features are provided on the connector and the arm connection portion, respectively. The axis of the arm member may coaxial with that of the main body.

In one aspect, the body and the arm member can form a variable angle between the body and the arm member. In such a case, the body and the arm member of the retractor can further include at least one stopping member configured to fix the angle between the body and the arm member. In some embodiments, the arm member may be integral with the main body. In either case, the axis of the arm member may form an angle, such as, for example, 30°, 45°, 60°, 90°, 120°, 135° 150°, or any angle therebetween, with respect to the axis of the main body.

In one aspect, the arm member and the main body may be made of stainless steel, aluminum, titanium, metal and/or polymer alloys, plastic materials and resin materials may also be used. The arm member and the main body may be fabricated by machining, forging, molding, and other manufacturing processes known in the art. The diameter of the main body can range, but is not limited to, from about 1 cm to about 5 cm or about 2.5 cm to about 3 cm, depending, for example, on the size of the work area, the size/length of the opening for accessing the work area, the size or number of structures being worked on, the size of the operator's hands, the amount of leverage needed in an operation, and the like. The arm member can have a length of, but is not limited to, about 1 cm to about 10 cm or about 3 cm to about 6 cm, depending, for example, on the size of the work area, the size/length of the opening for accessing the work area, the size or number of structures being worked on, the size of the operator's hands, the amount of leverage needed in an operation, and the like.

In one aspect, the arm member of the retractor can include a broadened portion between the first end and the second end. The broadened portion can take a number of forms depending on the intended application. For example, the broadened portion can be a substantially rectilinear flat portion projecting laterally from the arm member, a substantially flat portion having curved edges configured to fit a selected portion of the oral anatomy (e.g., the vestibular groove), a substantially curved portion configured to retract and cradle a portion of the patient's anatomy, or the like. In one aspect, the broadened portion can be configured for retraction of at least one of a lip portion and/or a portion of gum tissue during an oral surgical procedure.

In another embodiment, the present disclosure describes an instrument for field isolation during oral surgery. In one aspect, the instrument for field isolation during oral surgery can include a flexible dam membrane (e.g., a natural rubber dam, a flexible thermoplastic polymer dam, or a silicon rubber dam) having a periphery, a frame attached to the periphery of the membrane, with the frame being configured to fit one or more oral structures, and a retractor coupled to the frame of the flexible dam, the retractor being configured to position the flexible dam and/or retract lip tissues and/or gum tissues to expose a portion of an oral structure for treatment.

In one aspect, the frame of the flexible dam is configured to fit at least one periapical structure. In another aspect, the frame of the flexible dam is configured to fit in a vestibular groove. As discussed in greater detail elsewhere in this application, the frame can be configured to have a number of shapes and/or configurations in order to fit the at least one periapical structure, the vestibular groove, and/or another oral structure.

In another aspect, the flexible dam membrane can further include an apex gripping orifice. That is, the flexible dam membrane can include at least one structure such as, but not limited to, a cut-out portion configured to surround and isolate a portion of a tooth, such as, but not limited to, the apex portion of a tooth.

In yet another aspect, the instrument can further include a retaining member configured to retain the flexible dam around a root apex, the retaining member including a shaft having a first end, the first end including a first structure (e.g., a loop-shaped structure) configured to retain the apex gripping orifice of the flexible dam around the root apex.

In another embodiment, the present disclosure describes an instrument for isolation of a root apex during an oral procedure. In one aspect, the instrument for isolation of a root apex during an oral procedure can include a flexible dam membrane having a periphery, a frame attached to the periphery of the membrane, wherein the frame is configured to fit at least one periapical structure, a retractor coupled to the frame of the flexible dam, the retractor including a body and an arm member having an adjustable angle, the arm member being configured for positioning the flexible dam in proximity to the at least one periapical structure, and a widened portion positioned on the arm configured for refraction of at least one of lip tissues or gum tissues to expose the at least one periapical structure for treatment, and a retaining member configured to retain the flexible dam around the at least one periapical structure, the retaining member including a shaft having a first end, the first end including a first structure (e.g., a loop-shaped structure) configured to retain the flexible dam around the at least one periapical structure.

In one aspect, the at least one periapical structure can include a root apex. In another aspect, the at least one periapical structure can include a vestibular groove.

In one aspect, the shaft of the retaining member can further include a second end, the second end having a second structure (e.g., a loop-shaped structure) configured to retain the flexible dam around the at least one periapical structure.

In one aspect, the body and the arm member of the retractor each comprise a first end and a second end, with the first end of the arm member being configured to connect with a flexible dam, and the second end of the arm member being configured to pivotably connect with the first end of the body.

In one aspect, the retractor can further include a stopping member, such as a nut, a bolt, a ratcheting member and the like. In one aspect, the stopping member is configured to fix the angle between the body and the arm member. In another aspect, the stopping member can be configured to be actuated between a first position in which the second end of the arm member is released from the first end of the body, and a second position in which the second end of the arm member is secured to the first end of the body.

In another aspect where the refractor may be removably attached to the flexible dam, the retractor can include a main body of substantially cylinder shape with a first end and a second end, an arm member of substantially cylindrical shape with an arm body, an arm connection portion at one end thereof and an arm joint at the other end thereof. In some embodiments, the arm member can be attached to the main body at the first end thereof via an arm joint. The arm connection portion of the arm member can include a complementary configuration with the connector of the flexible dam, by means of which the arm member may be attached with the connector of the flexible dam. In some embodiments, a part is presented at the first end of the main body, to which the arm member is connected with the main body by means of the arm joint. In some embodiments, the part of the main body is formed by cutting or other machining process substantially along a longitudinal axis of the main body from the first end thereof towards the second end thereof over certain distance and forming a portion with a substantially semicircular section.

With such configuration, a face is formed in the main body substantially parallel with the axis of the main body. A thread hole is positioned in the face at a substantially central position of the part along the axis of the main body. The arm joint may have a complementary configuration with that of the part, i.e., a portion with a substantially semicircular section. Thus, another face is formed in the arm joint parallel with the axis of the arm member. A thread hole sized correspondingly to the hole formed in the main body is formed at a substantially center position in the opposite face of the arm joint along the axis of the arm member. The arm joint of the arm member may be connected and secured to the part of the main body by means of a stop member through the thread hole formed in the main body and the thread hole formed in the arm joint when they are aligned with each other. In some embodiments, the stop member is simply a bolt. The bolt has a handle portion that can be acted by a hand or a tool. In operation, the bolt is first actuated to a first position, in which the arm member may pivot with respect to the main body about the bolt so as to form an angle between the arm member and the main body, wherein angles can include but are not limited to 30°, 45°, 60°, 90°, 120°, 135°, 150°, or any angle therebetween. It should be noted that the stop member is not limited to the bolt. In some other embodiments, any other suitable device that can provide equivalent stopping effect, such as crimp member, may be used in place of the bolt.

Once the angle between the arm member and the main body, for example 120°, meets the user's needs, the bolt may be tightened to a second position, in which the arm member and the main body is securely held together by the aid of the friction between the face formed on the main body and the face formed on the arm joint under the pressure applied by the bolt. The angle between the arm member and the main body may be adjusted at any time by releasing the bolt to the first position, then tightening to the second position after adjustment. Thus, the different angle between the arm member and the main body will greatly expand the working range of the retractor. In some embodiments, materials improving friction may be formed or coated on at least one of the face formed on the main body and the face formed on the arm joint to enhance the friction between them as they remain at the second position.

In some further embodiments, the retractor can include a main body of substantially cylindrical shape with a first end and a second end; an arm member of substantially cylinder shape with an arm body, an arm connection portion at one end thereof and a ball joint at the other end thereof. The arm member is attached to the main body at the first end thereof by means of the ball joint. The arm connection portion of the arm member can include a complementary configuration with the connector of the flexible dam, by means of which the arm member may be engaged with the connector of the flexible dam. In this case, the main body is in the form of a hollow cylinder with an inner wall and an outer wall.

A cap can be positioned at the first end of the main body, which can include a hemispheric inner recess of the same diameter at the opening part with that of the inner wall of the main body. The cap may be attached to the main body, or may be integral with the main body. In either case, the inner wall of the main body may extend smoothly into the hemisphere inner recess of the cap. A slot is formed through the cap, which extends from where the cap meets the first end of the main body towards the top of the cap over a range of about 90°.

In some variant embodiments, the slot may extend more or less than 90°, including but not being limited to 45°, 60°, 120°, 135°, or 180°, or any degree in between. The width of the slot is adapted to receive the arm member. The ball joint of the arm member is adapted to fit within the hemispheric inner recess of the cap with the arm member protruding from the slot of the cap. Thus, the arm member is enabled to slide freely within the slot in order to form different angles between the arm member and the main body. Several discrete notches are formed in the ball joint in its surface opposed to the arm connection portion, which corresponds to the angle between the arm member and the main body, respectively.

A piston can be positioned within the main body, which can include a pressing part at one end thereof for pressing the ball joint of the arm member, a shaft part extending from the pressing part, and a handle removably connected to the other end of the piston. The pressing part is configured to be a cylinder shape having the same diameter with that of the inner wall of the main body. A reception recess can be formed in the pressing part where the pressing part contacts the ball joint of the arm member, which has a complementary shape with the contour of the ball joint, i.e., a concave hemisphere shape, in order to form a close contact therewith. A protrusion is formed in the reception recess of the pressing part of the piston, which is adapted to fit within one of the notches of the ball joint when assembled.

The second end of the main body can be open to outside, into which a plug may be removably attached by means of, for example, thread, interference fit, shape locking and the like. A center hole is formed in the plug, which is sized to admit the passage of the shaft part of the piston. In some embodiments of the retractor, a spring is positioned in the main body, which abuts at one end thereof against the pressing part oppose to the reception recess, and at the other end thereof against the plug in order to bias the piston towards the ball joint of the arm member. In operation, the piston is actuated to a first position against the force of the spring by pulling the handle, in which the protrusion of the piston is disengaged from the notch of the ball joint, whereby the angle between the arm member and the main body may be adjusted. Then the piston is released and biased back to a second position by the restoring force of the spring, in which the reception recess of the piston contacts the ball joint of the arm member and the protrusion of the piston is engaged again with one of the notches of the ball joint corresponding to the angle between the arm member and the main body, so as to keep the secured relations between the arm member and the main body.

In some embodiments of the retractor, the arm member, the main body, the piston and the plug may be made of stainless steel, although other suitable materials, for example, aluminum, titanium, plastic materials and resin materials may also be used. The outer diameter of the main body ranges, for example, but not limit to, from about 2.5 cm to about 3 cm, the inner diameter of the main body ranges, for example, but not limit to, from about 1.5 cm to about 2 cm, depending on particular applications. The arm member has a length of, for example, but not limited to, about 3 cm to about 6 cm, depending on particular applications. The width of the slot on the cap of the main body may range, for example, but not limit to, from about 0.7 cm to about 1 cm. Thus, the diameter of arm body of the arm member in this embodiment may be slightly less than the width of the slot in order to facilitate the movement of the arm member. For example, the diameter of the arm body of the arm member may be about 0.65 cm to about 0.95 cm corresponding to the width of the slot on the cap of the main body.

In some embodiments, the spring may be dispensed with, in which case, the pressing part of the piston may be provided with thread on its outer surface while a corresponding thread may be provided in the inner wall of the main body. Thus, the piston may be moved between the first position in which the ball joint of the arm member is released to admit adjustment of the angle between the arm member and the main body, and the second position in which the pressing part of the piston presses the ball joint of the arm member against the hemisphere recess of the cap so as to secure the angle between the arm member and the main body. In this case, the notch on the ball joint and the protrusion on the pressing part are also dispensable. In some embodiments, materials improving friction may be formed or coated on at least one of the surfaces of the ball joint of the arm member and the surface of the reception recess of the pressing part of the piston to enhance the friction between them as they remain at the second position.

In some further embodiments, the retractor may further include a broadened element attached to the arm member, which can be configured to isolate lip and gum tissues from the surgical field. The broadened element can include a plate portion of a substantially oblong shape, and a slide block attached to the plate portion at one side thereof. A hole is formed in the slide block parallel to the plate portion, which is adapted to the dimension of the arm body of the arm member so as to enable the broadened element freely slide on the arm body of the arm member. In some embodiments, a screw is provided in the slide block to act on the arm member when the broadened element is installed on the arm body of the arm member so as to position the slide block in different positions along the arm body of the arm member. In this embodiment, the shape and configuration of the slide block may be selected from cube, cylinder, and the like, provided that it may slide on the arm body to change the position of the broadened element along the arm body. The broadened element and the slide block may be made of stainless steel, aluminum alloy, plastic materials or resin materials, although other suitable materials, for example, titanium, may also be used.

In some embodiments, the broadened element may be integral with the arm body of the arm member, which may also simplify the manufacturing process and hence reduce the cost of the arm member.

Additionally, in yet some other embodiments, the retractor may further include at least one clip member positioned on the outer wall of main body along the axis of the main body. The clip member can be block shaped and have a channel extending parallel to the axis of the main body through the clip member. The channel is open to outside and the opening of the channel is sized to slightly less than its maximum dimension in order to receive and catch an additional device for providing assistance in the operation. The additional devices can include, but are not limited to, an optical fiber configured to provide lighting, a gas pipe configured to provide a dry air stream to the surgical site or a fluid pipe configured to provide flushing or irrigating liquid to the surgical site, and the like. The clip member may be made of plastic materials or resin materials, although other suitable materials, for example aluminum, stainless steel, copper may also be used.

Furthermore, in some embodiments, a texture feature, for example, knurling may be provided on the outer wall of the main body in order to improve grasping feel in operation. Alternatively, in some other embodiments, additional coating materials providing equivalent functions may be provided on the outer wall of the main body.

In yet another aspect of the medical devices described herein, a retaining member is provided, which comprises a shaft having a first end configured to retain a flexible dam around the root apex. In some other embodiments, the shaft of the retaining member has an operative member at the first end thereof configured to retain the flexible dam around the root apex. In some further embodiments, the shaft of the retaining member has an operative member at the second end thereof configured to retain the flexible dam around the root apex.

In this case, the operative member on both ends of the shaft may be same or different in shape or size with each other. The operative member may be integral with the shaft. Alternatively, the operative member may be formed separately and attached to the end of the shaft. In some embodiments, the operative member may have a flat oval shape sized to adapt to the root apex and surrounding structures. In some variant embodiments, the operative member may have a C-shape with a peripheral opening. The peripheral opening of the operative member may orient to any direction with respect to the shaft, depending on particular applications. In this embodiment of the retaining member, the radial dimension of the operative member may ranges, for example, but not limit to, from about 0.8 cm to about 1.2 cm while the thickness in the edge of the operative member may ranges, for example, but not limit to, from about 1 mm to about 2 mm, depending on particular applications. In some embodiments of the retaining member, the shaft and the operative member may be made of same materials, for example, stainless steel, plastic materials or resin materials when they are integrated with each other. In some other embodiments, if they are made separately, then they may be made of different materials. In particular, the shaft may be made of stainless steel, aluminum alloy, resin materials, although other suitable materials, for example, titanium may also be used. At the same time, the operative member may be made of stainless steel, aluminum alloy, resin materials or plastic materials, although other suitable materials, for example, titanium, ceramics, may also be used.

In some further embodiments of the retaining member, the shaft may have a portion in the vicinity of the operative member tapered towards the operative member. The portion may be in line with the shaft or may be deflected from the axis of the shaft so as to form an angle with respect to the shaft, which may be, for example, 90°, 120°, 135°, 150°, and 180°, or any degree in between.

As an aspect of the present disclosure, the flexible dam, the retractor or the retaining member may be used as a single instrument separately according to the specific applications. As another aspect of the disclosure, the flexible dam, the retractor and the retaining member may be grouped in any combination thereof as an instrument for providing field isolation during endodontic surgery, if desired.

In an aspect of the disclosure, a method of providing field isolation during an apical surgery using above mentioned the flexible dam, and/or the retractor and/or the retaining member is provided. The method comprises steps of stretching a flexible dam over the root apex to be treated; retracting the lip and gum tissues and the flexible dam using a retractor in such a manner that the root apex is exposed for treatment.

It should be understood that, other surgery operation may be performed using the flexible dam, and/or the refractor and/or the retaining member in a similar manner.

Before an apical surgery operation, the flexible dam, the refractor and the retaining member are sterilized. Next, the flexible dam is attached to the arm member of the refractor. In a case where the flexible dam is integral with the refractor, this step may be omitted.

If desired, an optical fiber can be attached to the clip member of the refractor that provides lighting for the operation. Other additional accessories, such as, but not limited to, a compressed air source configured to provide an air stream to the surgical site during the operation, or a water source configured to provide flushing or an irrigating liquid to the operation site during the operation may be used in a similar manner to the optical fiber.

In some embodiments, according to the position of the root apex to be treated, if the angle between the arm member and the main body of the retractor needs to be adjusted, the handle of the piston can be actuated to position the pressing part of the piston to the first position so as to release the ball join of the arm member relative to the hemispheric inner recess of the cap. Then, the arm member is adjusted to a desired orientation with respect to the main body of the retractor. In the following step, the handle is released, wherein the pressing part is returned back to press against the ball joint of the arm member under the restoring force of the spring to keep the fixed relation between the arm member and the main body of the retractor.

In some embodiments where lip and/or gum tissues may interfere with the operation, the broadened element may be positioned on the arm member in order to provide retraction of the lip and/or gum tissues. For example, the broadened element may be positioned on the arm member and affixed to the arm member by means of the screw or the like to prevent the lip and/or gum tissues from affecting the surgical operation.

Once the instrument is positioned in the mouth, the retractor may be used to position the flexible dam in such manner that the root apex is exposed for treatment. In some embodiments, with an apex gripping orifice provided in the flexible dam membrane, the retaining member may be used to retain the flexible dam over the root apex, providing field isolation. Optionally, in some other embodiments, if no such apex gripping orifice is provided in the flexible dam membrane, an incision can be made on the flexible dam membrane at the position corresponding to the root apex to be treated by using a blade or ophthalmic scissors to achieve the same effect.

With the flexible dam membrane isolating the root apex from surrounding environment, specific operations and treatment may be performed without concern that effusion of blood or other fluids in the surrounding environment or debris produced by the operation will affect the operation. After the operation, the retaining member can be removed followed by removing the retractor and the flexible dam member.

It should be understood that the above described method is illustrative in nature, and that it does not intends to limit the application of the flexible dam, the refractor and the retaining member in any way. Additionally, according to particular application, some steps in the method above may be dispensed. For example, the flexible dam may be disposable and be sterilized when manufactured and packaged. Thus, the sterilization of the flexible dam before a specific operation may be dispensed. This also applies to the refractor and the retaining member. Furthermore, in certain situations, it may be possible that the retaining member is not used to press the flexible dam membrane of the flexible dam. In this case, the cooperation of the flexible dam and the retractor may be used to secure flexible dam. From the above method, it should be understood that, for certain operations, the individual steps in above method may not be performed exactly in the order of description, or the method may include another steps to achieve other effects, depending on particular applications.

Several illustrative embodiments of respective aspects of present disclosure are given below by way of example with reference to the accompanying Figures. It should be noted, the following example are illustrative in nature.

Figure 1A:
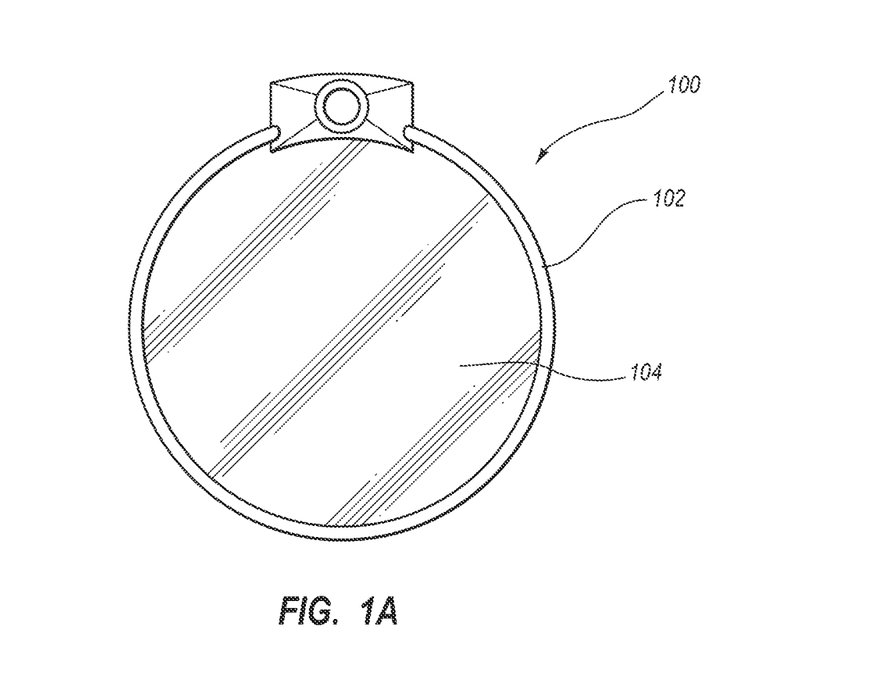
FIGS. 1A and 1B show a flexible member in accordance with an illustrative embodiment of a medical device.
Figure 1B:
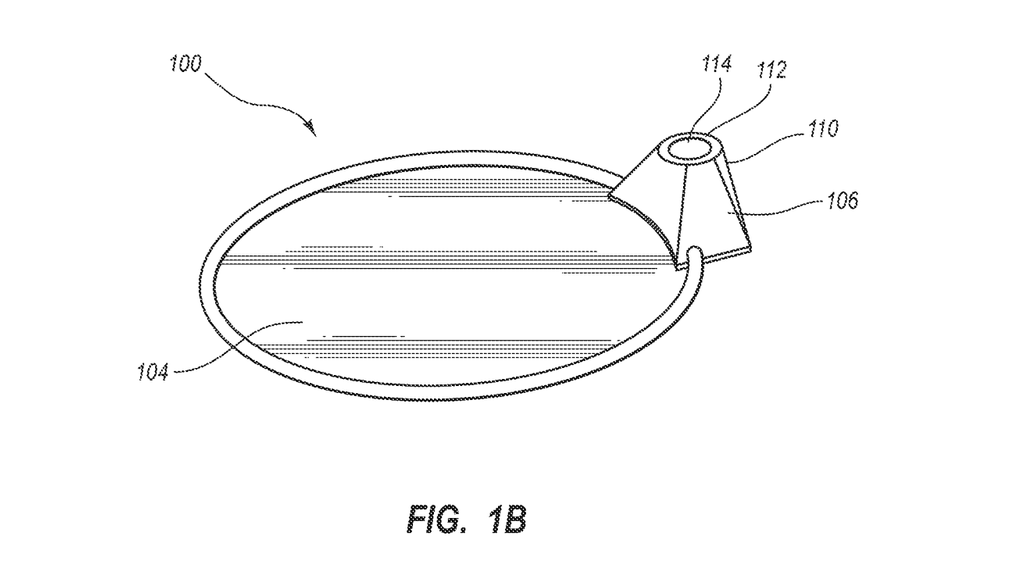

With reference to the accompanying Figures, FIGS. 1A and 1B illustrate a flexible member 100 (i.e., a flexible dam) according to one embodiment of the present disclosure. As illustrated, the flexible member 100 can include a frame 102 configured to fit one or more structures (e.g., periapical structures) to provide field isolation during an operation. The flexible member 100 further includes, a flexible dam membrane 104 stretched over the frame 102. In one embodiment, the flexible dam membrane 104 can include a membrane formed from a latex rubber membrane, a flexible thermoplastic polymer membrane, a silicone rubber membrane, or other suitable materials with suitable resilience and tension. In one aspect, the frame 102 may be made of same materials as the flexible dam membrane 104. However, in other aspects, the frame 102 may be made of a different material from that of the flexible dam membrane 104, such as metallic materials, which include but are not limited to aluminum, titanium, steel, alloy thereof, and the like, or plastic materials.

The frame 102 may be configured in a plane having a substantially circular cross-section, the diameter dimension of which may range, for example, from 1.5 cm to 3 cm. Alternatively, the frame may have other shapes including, but not being limited to, oval, square, oblong, triangle, trapezoid, and the like, depending on the particular application. In another embodiment, the frame 102 may be configured in a curved plane with a spatial profile to fit in the vestibular groove. In addition, the frame 102 may be shaped like a saddle, which has a middle plane and two wing planes extending at either end of the middle plane in a direction inclined with respect to the middle plane.

In an illustrative embodiment, the flexible member 100 may further include a retractor 110 configured to retract tissues in the region of the operation (e.g., lip and gum tissues in the case of an oral procedure) to provide field isolation in the region of the operation. For example, the flexible member 100 and the retractor 110 can be used to expose the root apex for treatment in order to provide field isolation during root end surgery.

In one embodiment, retractor may be a retracting member 106 integral with the frame 102, which is configured to retract lip and gum tissues and the flexible member 100 to expose the root apex for treatment. The refracting member 106 may be of a substantially cylindrical shape extending from the peripheral of the frame 102 substantially perpendicular to the plane of the frame 102. The length of the retracting member 106 may range, for example, from about 200 mm to about 300 mm.

In order to facilitate the operation by the flexible dam, an apex gripping orifice may be pre-formed in the flexible dam membrane 104, which is located substantially in the middle of flexible dam membrane 104. The apex gripping orifice may be sized slightly less than that of the root apex to be treated in order for the flexible dam membrane 104 to be tensioned around the root apex when the apex gripping orifice is slip over the root apex to be treated, so as to provide field isolation.

The materials used to make the flexible dam membrane 104 can include, but are not limited to, natural (i.e., latex) rubber, a flexible thermoplastic polymer, silicone rubber, medical rubber, or other suitable materials with suitable resilience and tension. In one embodiment, the frame 102 may be made of same materials as the flexible dam membrane 104. However, the frame 102 may also be made of different materials from that of the flexible dam membrane, such as metallic materials, such as, but not limited to, aluminum, titanium, steel, alloys thereof, and the like, or plastic materials. The flexible dam membrane 104 can be attached to the frame 102 by means of integral molding, melting, ultrasonic welding, or other means known by those skilled in the art.

In another illustrative embodiment, a retractor may be made separately from the flexible member 100 and removably attached to the flexible member 100 by means of a connector 112 located on the frame. In one aspect, the connector 112 may include a hole member 114 configured to receive a complementary member. In this case, several example configurations of the retractor are described hereafter with reference to the Figures. It should be understood by those skilled in the art that such example configuration of the refractor is given only for illustrative purpose, and are not meant to limit the scope of the disclosure in any manner.

Figure 2:
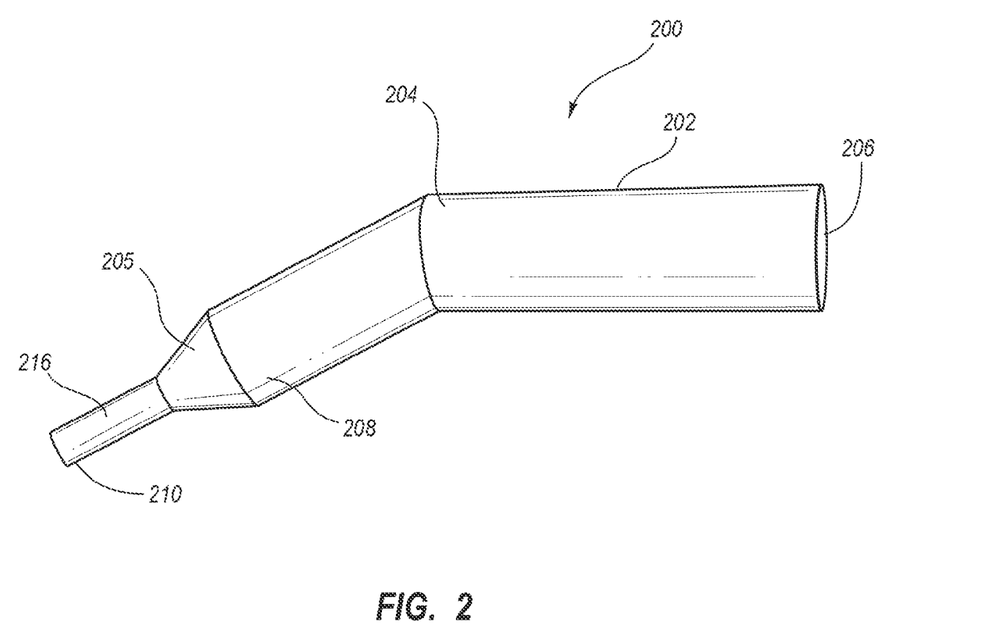
FIG. 2 shows a retractor in accordance with an illustrative embodiment of a medical device.

With reference to FIG. 2, an illustrative embodiment of a retractor 200 that can be removably attached to the flexible member 100 is shown. Retractor 200 can be employed instead of or in addition to retractor 110 shown in FIGS. 1A and 1B. In the illustrated embodiment, the retractor 200 includes a main body 202 of substantially cylindrical shape with a first end 204 and a second end 206, and an arm member 208 of substantially cylindrical shape with an arm body 216 and an arm connection portion 210 at one end thereof through an optional transition taper portion 205. The other end of the arm member 208 is attached with the main body 202 at the first end 204 thereof. The arm connection portion 210 of the arm member 208 can include a complementary configuration with the connector 112 (FIG. 1B), by means of which the arm member 208 may be engaged with the connector 112 of the flexible member 100. The manner for the connection of the connector 112 and the arm connection portion 210 may be threading, shape locking, and the like, depending on particular applications. In this case, corresponding connecting features are provided on the connector 112 and the arm connection portion 210, respectively. The axis of the arm member 208 may coaxial with that of the main body 202. As an variant embodiment, the axis of the arm member 208 may form an angle, such as, for example, 30°, 45°, 60°, 90°, 120°, 135°, 150°, or any degree in between, with respect to the axis of the main body 202. As a further variant embodiment, the arm member 208 may be integral with the main body 202. In this case, the arm member 208 and the main body 202 may be made of stainless steel, although other suitable materials, for example, aluminum, titanium, plastic materials and resin materials may also be used. The diameter of the main body 202 ranges from about 2.5 cm to about 3 cm, depending on particular applications. The arm member 208 has a length of about 3 cm to about 6 cm, depending on particular applications.

Figures 3A, 3B:
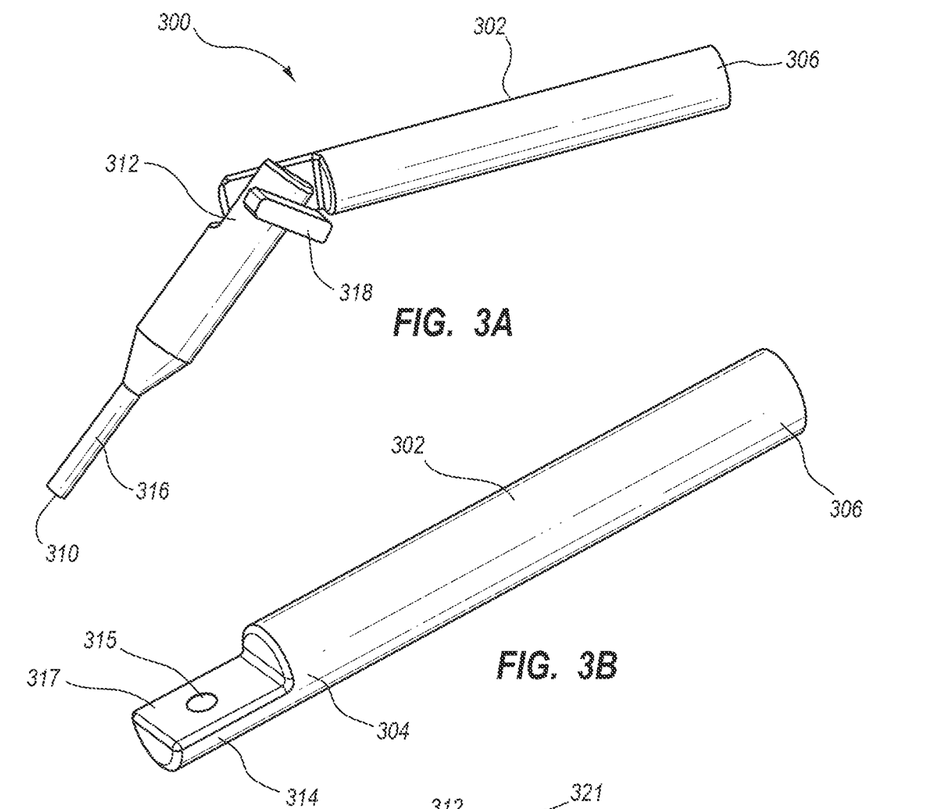
FIG. 3A shows a retractor in a perspective view.
FIG. 3B shows the main body of the retractor in a perspective view.
Figures 3C, 3D:
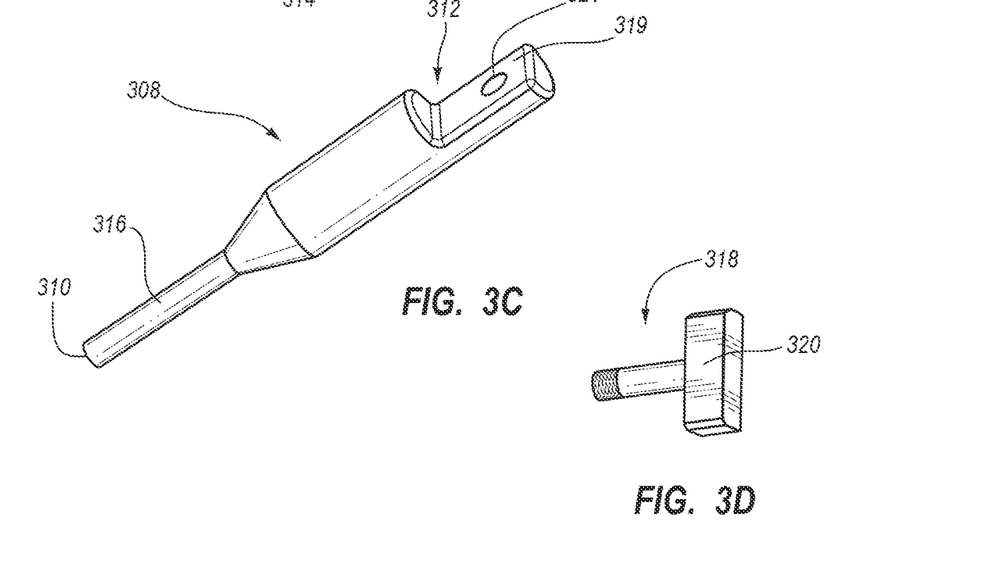
FIG. 3C shows an arm member of the retractor in a perspective view.
FIG. 3D shows a perspective view of a stop member of the retractor in accordance with an illustrative embodiment of a medical device.

In another embodiment of a retractor 300, as shown in FIGS. 3A-3D, the refractor 300 removably attached to the flexible member 100 (FIGS. 1A-1B) can include a main body 302 of substantially cylindrical shape with a first end 304 and a second end 306 as shown FIG. 3B, an arm member 308 of substantially cylinder shape with an arm body 316, an arm connection portion 310 at one end thereof and an arm joint 312 at the other end thereof as shown in FIG. 3C. The arm member 308 is attached to the main body 302 at the first end 304 thereof by means of the arm joint 312. The arm connection portion 310 of the arm member 308 can include a complementary configuration with the connector 112 of the flexible member 100, as shown in FIG. 1B, by means of which the arm member 308 may be attached with the connector 112 of the flexible member 100. A part 314 is presented at the first end 304 of the main body 302, to which the arm member 308 is connected with the main body 302 by means of the arm joint 312. The part 314 of the main body is formed by cutting or other machining process substantially along a longitudinal axis of the main body 302 from the first end 304 towards the second end 306 over a certain distance and forming a cylinder portion with a substantially semicircular section.

With such a configuration, a face 317 is formed parallel with the axis of the main body 302. A thread hole 315 is formed in the face 317 at a substantially central position of the part 314 along the axis of the main body 302. The arm joint 312 may have a complementary configuration with that of the part 314, i.e., a cylinder portion with a substantially semicircular section. Thus, another face 319 is formed parallel with the axis of the arm member 308. A thread hole 321 sized correspondingly to the hole 315 is formed at a substantially center position in the face 319 of the arm joint 312 along the axis of the arm member 308. The arm joint 312 of the arm member 308 may be connected and secured to the part 314 of the main body 302 by means of a stop member through the thread hole 315 and the thread hole 321 when they are aligned with each other. In this case, the stop member is simply a bolt 318 as shown in FIG. 3D. The bolt 318 has a handle portion 320 that can be acted by a hand or a tool, as shown in FIG. 3A. In operation, the bolt 318 is first actuated to a first position, in which the arm member 308 may pivot with respect to the main body 302 about the bolt 318 so as to form an angle between the arm member 308 and the main body 302. Suitable angles can include, but are not limited to, 30°, 45°, 60°, 90°, 120°, 135° 150°, or any angle therebetween. It should be noted that the stop member is not limited to the bolt 318. Any other suitable device that can provide equivalent stopping effect, such as crimp member, may be used in place of the bolt 318.

Once the angle between the arm member 308 and the main body 302, for example 120°, meets the requirement, the bolt 318 may be tightened to a second position, in which the arm member 308 and the main body 302 are securely held together by the aid of the friction between the face 317 and the face 319 under the pressure applied by the bolt 318. The angle between the arm member 308 and the main body 302 may be adjusted at any time by releasing the bolt 318 to the first position, then tightening to the second position after adjustment. Thus, the different angle between the arm member 308 and the main body 302 will greatly expand the working range of the refractor 300. In an illustrative embodiment, friction improving elements, such as, but not limited to, texturing, knurling, abrasive materials, combinations thereof, and the like may be disposed, formed, or coated on at least one of the face 317 and the face 319 to enhance the friction between them as they remain at the second position.

Similar to the first illustrative embodiment of the retractor 300, the arm member 308 and the main body 302 may be made of stainless steel, although other suitable materials, for example, aluminum, titanium, plastic materials or resin materials may also be used. The diameter of the main body 302 ranges from about 2.5 cm to about 3 cm, depending on particular applications. The arm member 308 has a length of about 3 cm to about 6 cm, depending on particular applications.

Figure 4A:
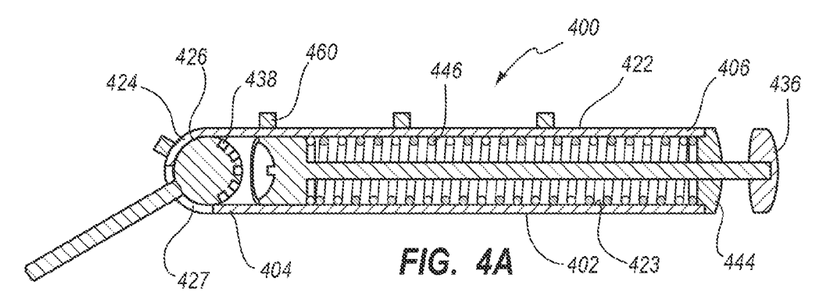
FIG. 4A shows a partial cut-away view of a retractor.
Figure 4B:
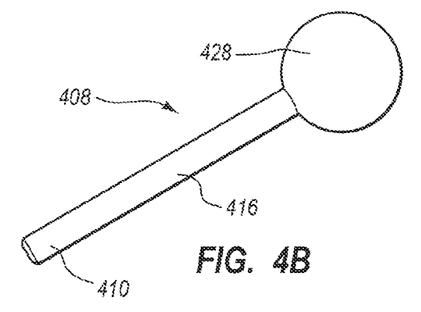
FIG. 4B shows an arm member, the FIG. 4C shows a piston of the retractor.

In a third illustrative embodiment, as shown in FIG. 4A, the retractor 400 can include a main body 402 of substantially cylindrical shape with a first end 404 and a second end 406; an arm member 408 of substantially cylindrical shape with an arm body 416, an arm connection portion 410 at one end thereof and a ball joint 428 at the other end thereof, as shown in FIG. 4B. The arm member 408 is attached to the main body 402 at the first end 404 thereof by means of the ball joint 428. The arm connection portion 410 of the arm member 408 can include a complementary configuration with the connector 112 of the flexible member 100, as shown in FIG. 1B, by means of which the arm member 408 may be engaged with the connector 112 of the flexible member 100. In this case, the main body 402 is in the form of a hollow cylinder with an inner wall 423 and an outer wall 422.

A cap 424 is positioned at the first end 404 of the main body as shown in FIG. 4A, which can include a hemispheric inner recess 426 of the same diameter at the opening part with that of the inner wall 423 of the main body 402. The cap 424 may be attached to the main body 402, or may be integral with the main body 402. In either case, the inner wall 423 of the main body 402 may extend smoothly into the hemispheric inner recess 426 of the cap 424. A slot 427 is formed through the cap 424, which extends from where the cap 424 meet the first end 404 of the main body towards the top of the cap 424 over a range of about 90° as shown in FIG. 4A.

In an variant embodiment, the slot 427 may extends more or less than 90°, including but not being limited to 45°, 60°, 120°, 135°, or 180°, or any angle therebetween. The width of the slot 427 is adapted to receive the arm member 408. The ball joint 428 of the arm member 408 is adapted to fit within the hemisphere inner recess 426 of the cap 424 with the arm member 408 protruding from the slot 427 of the cap 424. Thus, the arm member 408 is enabled to slide freely within the slot 427 in order to form different angles between the arm member 408 and the main body 402. Several discrete notches 438 are formed in the ball joint 428 in its surface opposite to the arm connection portion 410, which corresponds to the angle between the arm member 408 and the main body 402, respectively.

Figure 4C:
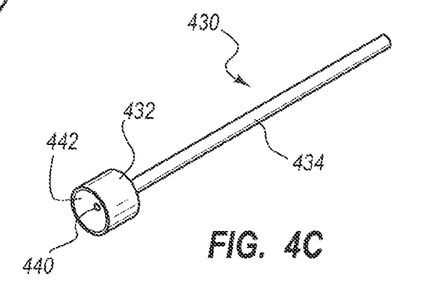

A piston 430 is positioned within the main body 402, which can include a pressing part 432 at one end thereof for pressing the ball joint 428 of the arm member 408, a shaft part 434 extending from the pressing part 432, and a handle 436 (FIG. 4A) removably connected to the other end of the piston 430, as shown in FIG. 4C. The pressing part 432 can be configured with a cylindrical shape having the same diameter of the inner wall 423 of the main body 402. A reception recess 442 is formed in the pressing part 432 where the pressing part 432 contacts the ball joint 428 of the arm member 408, which has a complementary shape with the contour of the ball joint 428, i.e., a concave hemispheric shape, in order to form a close contact therewith. A protrusion 440 is formed in the reception recess 442 of the pressing part 432 of the piston 430, which is adapted to fit within one of the notches 438 of the ball joint 428 when assembled, as shown in FIG. 4A.

As shown in FIG. 4A, the second end 406 of the main body 402 is open to outside, into which a plug 444 may be removably attached by means of, for example, thread, interference fit, shape locking and the like. A center hole is formed in the plug 444, which is sized to admit the passage of the shaft part 434 of the piston 430. With reference to FIG. 4A showing the assembled retractor 400, a spring 446 is positioned in the main body 402 as shown in FIG. 4A, which abuts at one end thereof against the pressing part 432 opposite to the reception recess 442, and at the other end thereof against the plug 444 in order to bias the piston 430 towards the ball joint 428 of the arm member 408. In operation, the piston 430 is actuated to a first position against the force of the spring 446 by pulling the handle 436, in which the protrusion 440 of the piston 430 is disengaged from the notch 438 of the ball joint 428, whereby the angle between the arm member 408 and the main body 402 may be adjusted. Then the piston 430 is released and biased back to a second position by the restoring force of the spring 446, in which the reception recess 442 of the piston 430 contacts the ball joint 428 of the arm member 408 and the protrusion 440 of the piston 430 is engaged again with one of the notches 438 of the ball joint 428 corresponding to the angle between the arm member 408 and the main body 402, so as to keep the secured relations between the arm member 408 and the main body 402.

In this embodiment of the retractor 400, the arm member 408, the main body 402, the piston 430 and the plug 444 may be made of stainless steel, as described in the first illustrative embodiment, although other suitable materials, for example, aluminum, titanium, plastic materials and resin materials may also be used. The outer diameter of the main body 402 ranges from about 2.5 cm to about 3 cm, the inner diameter of the main body 402 ranges from about 1.5 cm to about 2 cm, depending on particular applications. The arm member 408 has a length of about 3 cm to about 6 cm, depending on particular applications. The width of the slot 427 on the cap 424 of the main body 402 may ranges from about 0.7 cm to about 1 cm. Thus, the diameter of arm body 416 of the arm member 408 in this embodiment may be slightly less than the width of the slot 427 in order to facilitate the movement of the arm member 408. For example, the diameter of the arm body 416 of the arm member 408 may be about 0.65 cm to about 0.95 cm corresponding to the width of the slot 427 on the cap 424 of the main body 402.

In a variant embodiment that is not shown, the spring 446 may be dispensed with, in which case the pressing part 432 of the piston 430 may be provided with thread on its outer surface while a corresponding thread may be provided in the inner wall 423 of the main body. Thus, the piston 430 may be moved between the first position in which the ball joint 428 of the arm member 408 is released to permit adjustment of the angle between the arm member 408 and the main body 402, and the second position in which the pressing part 432 of the piston 430 presses the ball joint 428 of the arm member 408 against the inner recess 426 of the cap 424 so as to secure the angle between the arm member 408 and the main body 402. In this case, the notch 438 on the ball joint 428 and the protrusion 440 on the pressing part 432 are also dispensable. As described previously, materials improving friction may be formed or coated on at least one of the surface of the ball joint 428 of the arm member 408 and the surface of the reception recess 442 of the pressing part 432 of the piston 430 to enhance the friction between them as they remain at the second position.

Figure 4D:
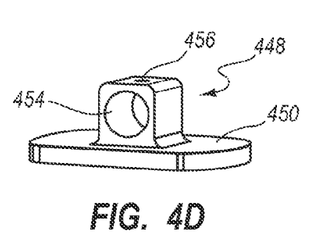
FIG. 4D shows a broadened element of the retractor.

In a further illustrative embodiment of the retractor 400, the retractor 400 may further include a broadened element 448 attached to the arm member 408, which is configured to isolate lip and gum tissues from the surgical field, as shown in FIG. 4D. The broadened element 448 can include a plate portion 450 of a substantially oblong shape. A hole 454 is formed in the broadened element 448 parallel to the plate portion 450, which is adapted to the dimension of the arm body 416 of the arm member 408 so as to enable the broadened element 448 freely slide on the arm body 416 of the arm member 408. A screw 456 is provided in the broadened element 448 to act on the arm member 408 when the broadened element 448 is installed on the arm body 416 of the arm member 408 so as to position the broadened element 448 in different positions along the arm body 416 of the arm member 408. In this embodiment, the shape and configuration of the plate portion 450 may be selected from cube, cylinder, and the like, provided that it may slide on the arm body 416 to change the position of the broadened element 448 along the arm body 416. The broadened element 448 and the plate portion 450 may be made of stainless steel, aluminum alloy, plastic materials or resin materials, although other suitable materials, for example, titanium, may also be used.

In one embodiment, the broadened element 448 may be integral with the arm body 416 of the arm member 408, which may also simplify the manufacture process and hence reduce the cost of the arm member 408.

Figure 4E:
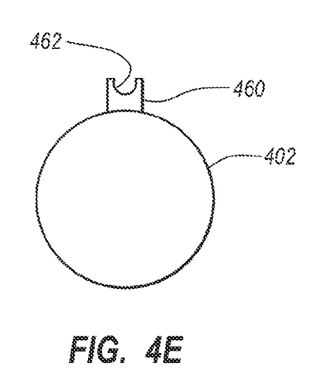
FIG. 4E shows a clip member of the refractor in accordance with an illustrative embodiment of a medical device.

Additionally, in yet another illustrative embodiment, the retractor 400 may further include at least one clip member 460 positioned on the outer wall 422 of main body 402 along the axis of the main body 402, as shown in FIG. 4E. The clip member 460 is shaped of a block, and has a channel 462 extending parallel to the axis of the main body through the clip member 460. The channel 462 is open to outside and the opening of the channel 462 is sized to slightly less than its maximum dimension in order to receive and catch an additional device for providing assistance in the operation. The additional devices can include, but are not limited to, optical fibers configured to provide lighting, a gas pipe configured to provide blowing dry air source, or a fluid pipe configured to provide a flushing liquid, and the like. The clip member 460 may be made of plastic materials or resin materials, although other suitable materials, for example aluminum, stainless steel, copper may also be used.

Furthermore, a texture feature, for example, knurling or an abrasive material, may be provided on the outer wall 422 of the main body 402 in order to improve grasping feel in operation. Alternatively, additional coating materials providing equivalent functions may be provided on the outer wall 422 of the main body 402.

Figure 5:
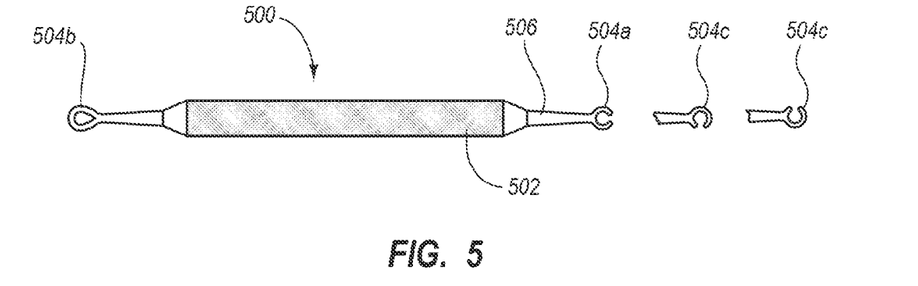
FIG. 5 shows a retaining member in accordance with an illustrative embodiment of a medical device.

In another aspect of the disclosure, a retaining member 500 is provided, as shown in FIG. 5, which can include a shaft 502, and an operative member 504a at one end of the shaft 502 configured to retain the flexible dam around the root apex. As an alternative, the shaft 502 may have a second operative member 504b at the other end of the shaft. In this case, the operative members 504a and 504b on both ends of the shaft 502 may be same or different in shape or size with each other. The operative members 504a and 504b may be integral with the shaft 502. Alternatively, the operative members 504a and 504b may be formed separately and attached to the end of the shaft 502. The operative member may have a flat oval shape sized to adapt to the root apex and surrounding structures as seen at 504b. In a variant embodiment, the operative member may have a C-shape with a peripheral opening as seen at 504a and 504c. The peripheral opening of the operative member 504c may orient to any direction with respect to the shaft 502, depending on particular applications. A collection of multiple and/or varying operative members together with a corresponding shaft and/or other parts of a corresponding medical instrument may form a kit. In this embodiment of the retaining member 500, the radial dimension of the operative members 504a, 504b, or 504c may ranges from about 0.8 cm to about 1.2 cm while the thickness in the edge of the operative members 504a, 504b, or 504c may range from about 1 mm to about 2 mm, depending on particular applications. In this embodiment of the retaining member 500, the shaft 502 and the operative members 504a, 504b, or 504c may be made of the same materials, for example, stainless steel, plastic materials or resin materials when they are integrated with each other. If they are made separately, then they may be made of different materials. In particular, the shaft 502 may be made of stainless steel, aluminum alloy, resin materials, although other suitable materials, for example, titanium may also be used. At the same time, the operative member 504 may be made of stainless steel, aluminum alloy, resin materials or plastic materials, although other suitable materials, for example, titanium, ceramics, may also be used.

Figure 6:
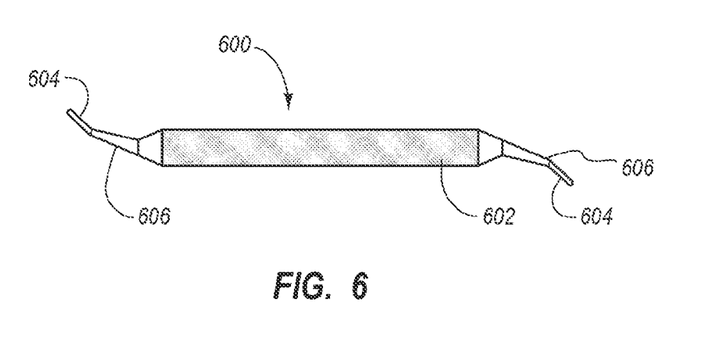
FIG. 6 shows a retaining member in accordance with an illustrative embodiment of a medical device.

In a further illustrative embodiment of the retaining member 600, the shaft 602 may have a tapered portion 606 in the vicinity of the operative member 604 tapered towards the operative member 604, as shown in FIG. 6. The tapered portion 606 may be in line with the shaft 602 or may be deflected from the axis of the shaft so as to form an angle with respect to the shaft, which may be, for example, 90°, 120°, 135°, 150°, and 180°, or any angle therebetween, as shown in FIG. 6.

In one aspect of the disclosure, a method of providing field isolation during an apical surgery using above mentioned the flexible dam, and/or the retractor and/or the retaining member will be described below with reference FIG. 7. It should be understood that, other surgery operation may be performed using the flexible dam, and/or the retractor and/or the retaining member in a similar manner with those described below. The following method is carried out using the flexible dam, the third illustrative embodiment of the retractor, and the retaining member, which is given by way of example.

Example

Figure 7:
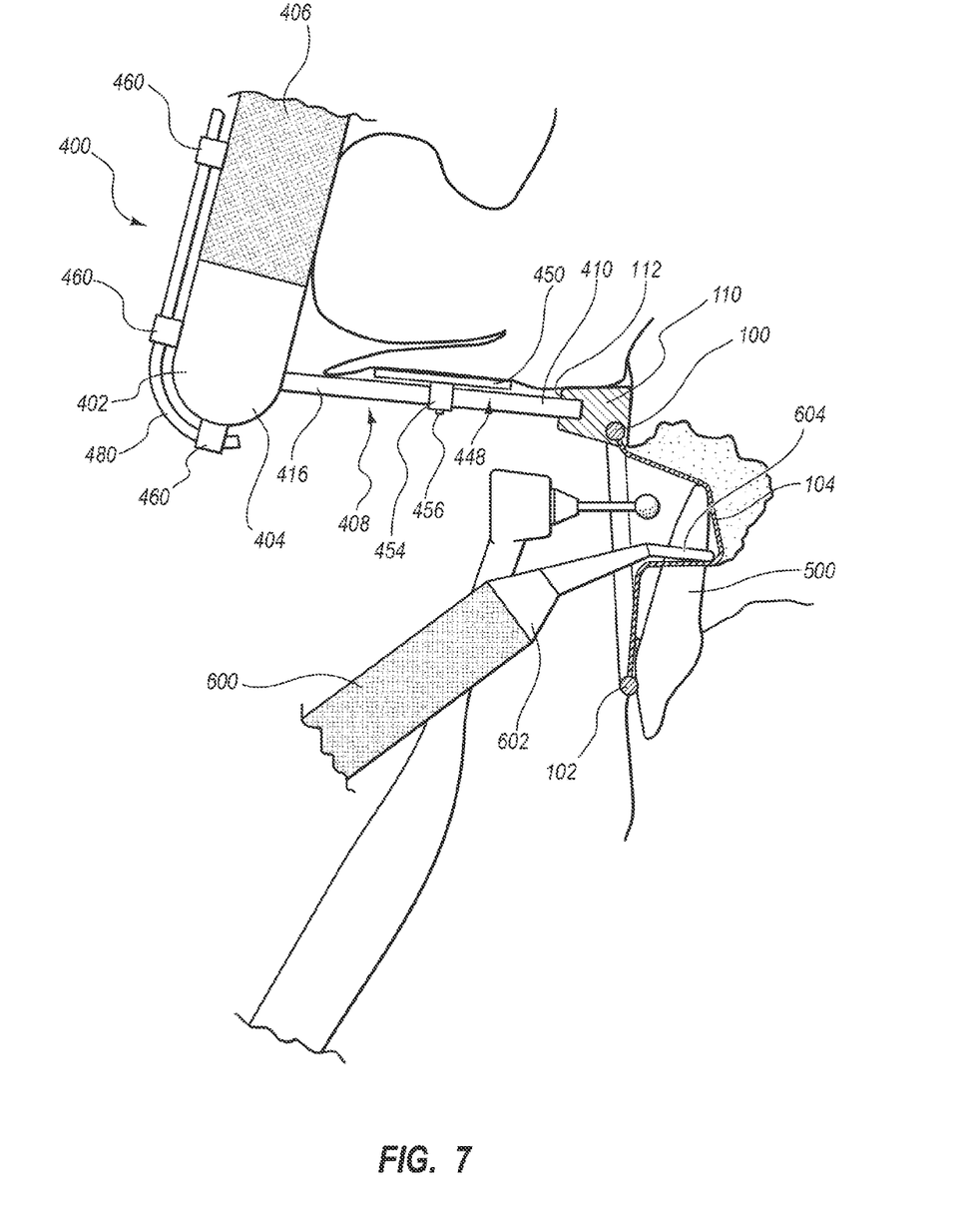
FIG. 7 is a perspective view of the implementation of a flexible dam, a refractor and a retaining member in accordance with an illustrative embodiment of a medical device.

As shown in FIG. 7, a specific implementation example is given for the purpose of illustration. For sake of clarity, those components not shown in FIG. 7 are not duplicated, detail of which may be referred to relevant contents described herebefore. In this example, the flexible member 100 can include a frame 102 configured to fit periapical structures, a flexible dam membrane 104 stretched over the frame 102. The frame 102 may be configured in a plane shaped of circular in cross section. A connector 112 is located on the frame 102, by means of which the flexible member 100 is connected with a retractor 400. An apex gripping orifice may be preformed in the flexible dam membrane 104, which may be located substantially in the middle of flexible dam membrane 104.

A refractor 400 in accordance with the third illustrative embodiment as described above can include a main body 402 of substantially cylindrical shape with a first end 404 and a second end 406; an arm member 408 of substantially cylindrical shape with an arm body 416, an arm connection portion 410 at one end thereof and a ball joint at the other end thereof, as shown in FIG. 4B at 428. The arm member 408 is attached to the main body 402 at the first end 404 thereof by means of the ball joint 428. The arm connection portion 410 of the arm member 408 can include a complementary configuration with the connector 112 of the flexible member 100, as shown in FIG. 1B, by means of which the arm member 408 may be engaged with the connector 112 of the flexible member 100.

The retractor 400 can include a broadened element 448 attached to the arm member 408, which is configured to isolate lip and gum tissues from the surgical field. The broadened element can be seen more clearly in FIG. 4D, for example. As seen in FIG. 4D, The broadened element 448 can include a plate portion 450 of a substantially oblong shape, and a sliding member such as, but not limited to, hole 454 attached to the plate portion 450 at one side thereof. The broadened element 448 may be secured along the arm member 408 by means of the screw 456 or another fastener in order to isolate lip and gum tissues from the root apex to be treated in the surgical field.

The refractor 400 can include one or more clip members 460 positioned on the outer wall 422 of main body 402 along the axis of the main body 402, as shown in FIG. 4E. In the illustrated embodiment, an optical fiber 480 is fixed in the clip members 460 and oriented to the root apex to be treated in order to provide lighting during the operation. One will appreciate that the clip members 460 can be usefully employed to affix any number of useful instruments to the retractor 400. For example, the clip members 460 can be used to affix a line used for directing a dry air stream, a water source, or an adhesive curing light into the oral cavity during an operation.

As shown in FIG. 7, a retaining member 600 can include a shaft 602, and an operative member 604 at an end of the shaft 602 configured to retain the flexible dam membrane 104 around the root apex 500. The operative member 604 is deflected from the axis of the shaft so as to form an angle with respect to the shaft 602. For example, in the illustrated embodiment, as shown in FIG. 6, portion 606 is deflected from the axis of the shaft 602 so as to form an angle of about 150° with respect to the shaft 602. One will appreciate, however, that other angles may be usefully employed in other embodiments.

As shown in FIG. 7, the flexible member 100 is attached to the arm member 408 of the retractor 400 by means of the connector 112. Due to the position of the root apex 500 to be treated shown in FIG. 7, the angle between the arm member 408 and the main body 402 of the retractor 400 is adjusted and secured to almost 90° with the flexible dam membrane 104 of the flexible member 100 substantially parallel with the extension direction of the root apex to be treated. With an apex gripping orifice provided in the flexible dam membrane 104, the retaining member 600 is used to press the flexible dam membrane 104 with its operative member 604 to sleeve the apex gripping orifice around the root apex to be treated, in which case the flexible dam membrane 104 closely encloses the root apex to be treated under tension produced by itself, providing field isolation. With the flexible dam membrane 104 isolating the root apex from surrounding environment, specific operation and treatment can be performed without concern that effusion of blood or other fluids in the surrounding environment or debris produced by the operation will affect the operation.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B".

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

As used herein, the term "substantially" is used to mean to a great extent or degree. The term "substantially" is often used in conjunction with another term to describe the extent or degree of that term such as, but not limited to, angles, shapes, and states of being. For example, the term "substantially perpendicular" may be used herein to indicate some degree of leeway in an angular measurement. That is, an angle that is "substantially perpendicular" may be 90°, but angles such as 45°, 60°, 65°, 70°, 75°, 80°, 85°, 95°, 100°, 105°, 110°, 115°, 120°, 125°, 130, or 135° may also be considered to be "substantially perpendicular." Similarly, "substantially" may be used in conjunction with a shape term such as "substantially cylindrical" to indicate that the object referred to may have a circular profile or an ovoid profile. Likewise, a term describing a state of being such as the term "substantially closed," may be used to indicate that something is mostly closed or usually closed, but that it need not be 100% closed or always closed.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

The invention claimed is:

1. An instrument for isolation of a root apex during an oral procedure, comprising:
a flexible membrane;
a frame encompassing an outer periphery of the flexible membrane, the frame being configured to fit at least one periapical structure;
a connector positioned on the frame and including an aperture therein;

a retractor including a body and an arm member, the arm member having a first end and a second end opposite the first end, wherein the first end is configured to be pivotally connected to the body to enable adjustment of an angle between the body and the arm member and wherein the second end is configured to be coupled to the aperture to enable use of the arm member to position the flexible membrane in proximity to the at least one periapical structure; and a retaining member configured to retain the flexible dam around the at least one periapical structure, the retaining member including a shaft having a first end, the first end including a first structure configured to retain the flexible dam around the at least one periapical structure.

2. The instrument of claim 1, wherein the shaft of the retaining member further includes a second end having a tapered structure extending at an angle with respect to the shaft and configured to retain the flexible membrane around the at least one periapical structure.

3. The instrument of claim 1, wherein the retractor further comprises a stopping member configured to fix the angle between the body and the arm member.

4. The instrument of claim 1, wherein the retractor extends outwardly from the frame in a second plane different from a first plane defined by the frame.

* * * * *

UNITED STATES PATENT AND TRADEMARK OFFICE
CERTIFICATE OF CORRECTION

PATENT NO. : 8,480,574 B2
APPLICATION NO. : 12/770120
DATED : July 9, 2013
INVENTOR(S) : Li It is certified that error appears in the above-identified patent and that said Letters Patent is hereby corrected as shown below:

In the Specification

In Column 1, Line 40, delete "refractor" and insert -- retractor --, therefor.

In Column 2, Line 22, delete "refractor" and insert -- retractor --, therefor.

In Column 2, Line 30, delete "refractor" and insert -- retractor --, therefor.

In Column 5, Line 64, delete "refraction" and insert -- retraction --, therefor.

In Column 6, Line 26, delete "refractor" and insert -- retractor --, therefor.

In Column 10, Line 25, delete "refractor" and insert -- retractor --, therefor.

In Column 10, Line 36, delete "refractor" and insert -- retractor --, therefor.

In Column 10, Line 39, delete "refractor" and insert -- retractor --, therefor.

In Column 10, Line 40, delete "refractor." and insert -- retractor. --, therefor.

In Column 10, Line 41, delete "refractor," and insert -- retractor, --, therefor.

In Column 10, Line 44, delete "refractor" and insert -- retractor --, therefor.

In Column 11, Line 25, delete "refractor" and insert -- retractor --, therefor.

In Column 11, Line 31, delete "refractor" and insert -- retractor --, therefor.

In Column 12, Line 19, delete "refracting" and insert -- retracting --, therefor.

Signed and Sealed this
Third Day of December, 2013

Margaret A. Focarino
*Commissioner for Patents of the United States Patent and Trademark Office*

CERTIFICATE OF CORRECTION (continued)
U.S. Pat. No. 8,480,574 B2

In Column 12, Line 55, delete "refractor" and insert -- retractor --, therefor.

In Column 13, Line 26, delete "refractor" and insert -- retractor --, therefor.

In Column 14, Lines 16-17, delete "refractor" and insert -- retractor --, therefor.

In Column 18, Line 7, delete "refractor" and insert -- retractor --, therefor.

In Column 18, Line 32, delete "refractor" and insert -- retractor --, therefor.